United States Patent [19]

Bates

[11] Patent Number: 4,702,740
[45] Date of Patent: Oct. 27, 1987

[54] COLLECTION SYSTEM WITH VALVE MEMBERS

[75] Inventor: David A. Bates, Libertyville, Ill.
[73] Assignee: The Kendall Company, Boston, Mass.
[21] Appl. No.: 400,529
[22] Filed: Jul. 21, 1982
[51] Int. Cl.⁴ .............................................. A61M 1/00
[52] U.S. Cl. .................................... 604/323; 604/335
[58] Field of Search ................ 604/317, 319, 322–327, 604/331, 335, 350; 128/760–762, 766–768; 137/614.11, 614.13, 614.14; 251/9; 222/428, 429, 452; 417/571

[56] References Cited

U.S. PATENT DOCUMENTS

| | | | |
|---|---|---|---|
| 3,865,165 | 2/1975 | Glass | 604/323 |
| 3,904,326 | 9/1975 | Clement | 417/571 |
| 4,386,930 | 6/1983 | Cianci | 604/317 |

OTHER PUBLICATIONS

The Random House Dictionary of the English Language, Stein, Random House, Inc. New York, "Valve", p. 1579, 1966.

*Primary Examiner*—C. Fred Rosenbaum
*Assistant Examiner*—J. L. Kruter
*Attorney, Agent, or Firm*—Powell L. Sprunger

[57] ABSTRACT

A collection system for body fluids comprising, a receptacle having a collection chamber for retaining the body fluids, a first container having a supply chamber for retaining a bactericide, and a second container having a holding chamber, with the holding chamber being located above a lower portion of the collection chamber, and the supply chamber being located above a lower portion of the holding chamber. The system has a first valve member permitting the passage of bactericide from the supply chamber into the holding chamber, and a second valve member permitting the passage of the bactericide from the holding chamber into the collection chamber.

11 Claims, 3 Drawing Figures

COLLECTION SYSTEM WITH VALVE MEMBERS

BACKGROUND OF THE INVENTION

The present invention relates to collection systems for urine.

Urine drainage systems of the type comprising a catheter and collection receptacle are known. In such systems, a distal end of the catheter is passed through the urethra of a patient until it is located in the bladder, with a proximal end of the catheter being located outside the patient's body. An upstream end of a drainage tube is connected to the proximal end of the catheter, and a downstream end of the drainage tube communicates with a collection chamber in the receptacle. In use, urine drains through a drainage eye in the distal end of the catheter, and through the catheter and drainage tube into the collection chamber for retention therein.

Since such systems are closed to the atmosphere, contamination of the systems is minimized. However, it has been found that bacteria may grow in the collected urine in the receptacle, and may move in retrograde fashion to the patient's bladder resulting in possible harm to the patient. It has been attempted to introduce a bactericide into the collection chamber at periodic intervals, and the bactericide minimizes the possibility of bacteria growth in order to solve this problem. However, in prior devices separate loose containers of the bactericide are required, resulting in retention of extra parts and inconvenience to hospital personnel. Also, the bactericide has been introduced through a slit in a rubber plug which poses a risk of contamination in the receptacle.

SUMMARY OF THE INVENTION

A principal feature of the present invention is the provision of an improved collection system of simplified construction.

The collection system of the invention comprises, a receptacle having a collection chamber for retaining the body fluids, and a drainage tubular section of flexible material communicating with the collection chamber. The system has a first container having a supply chamber for retaining a bactericide, and a second container having a holding chamber, with the holding chamber being located above a lower portion of the collection chamber, and with the supply chamber being located above a lower portion of the holding chamber. The system has clamping apparatus comprising first and second clamp members, including means for pivoting central portions of the first and second clamp members, with first and second end portions of the first and second clamp members extending from the central portions. The tubular section is received between the first end portions of the first and second clamp members. The clamping apparatus is movable between a first position with the first end portions being substantially spaced and the second end portions being closely spaced, and a second position with the first end portions being closely spaced and the second end portions being substantially spaced. The system has first valve means, and second valve means.

A feature of the present invention is that the tubular section is substantially open to permit drainage of liquid from the receptacle at the first position of the first and second clamp members.

Another feature of the invention is that the tubular section is closed to prevent passage of liquid through the tubular section at the second position of the first and second clamp members.

Yet another feature of the invention is that the first valve means opens to permit passage of the bactericide from the supply chamber into the holding chamber responsive to movement of the clamping apparatus to the first position.

Still another feature of the invention is that the first valve means closes to prevent passage of the bactericide from the holding chamber into the supply chamber responsive to movement of the clamping apparatus to the second position.

Yet another feature of the invention is that the second valve means opens to permit passage of the bactericide from the holding chamber into the collection chamber responsive to movement of the clamping apparatus to the second position.

A further feature of the invention is that the second valve means closes to prevent passage of the contents of the collection chamber into the holding chamber responsive to movement of the clamping apparatus to said first position.

Thus, a feature of the present invention is that a quantity of the bactericide is automatically injected into the collection chamber when the contents of the receptacle is emptied through the tubular section.

Further features will become more fully apparent in the following description of the embodiments of this invention and from the appended claims.

DESCRIPTION OF THE PREFERRED EMBODIMENTS

Figure 1:
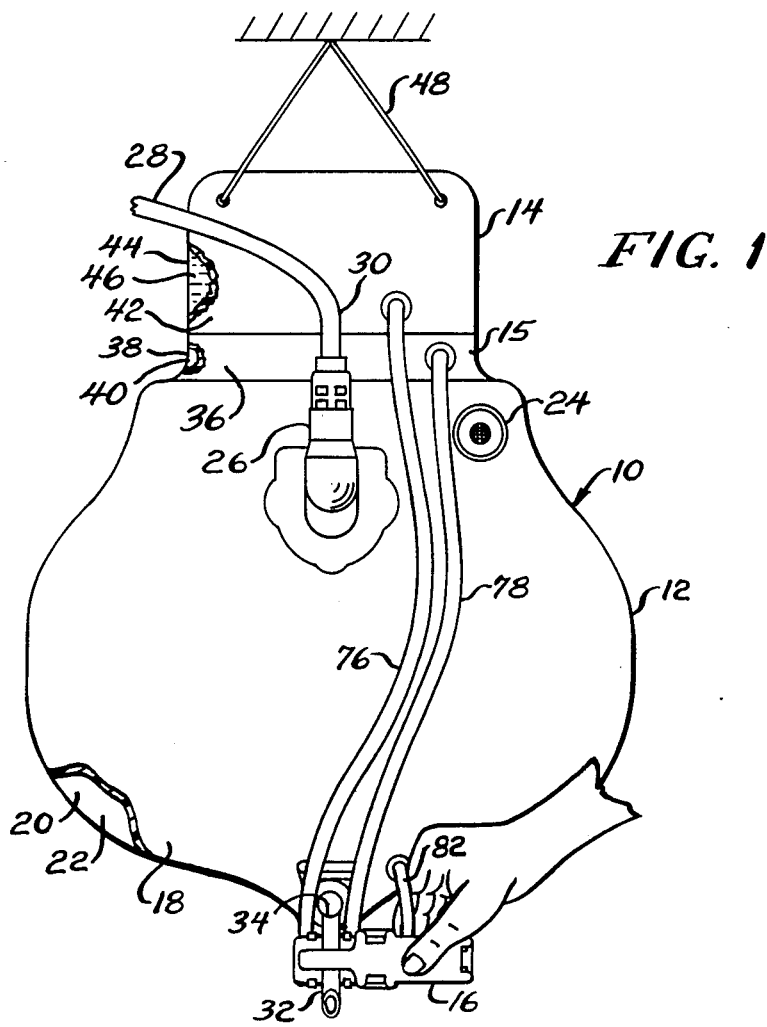
FIG. 1 is a fragmentary front elevational view of a collection system of the present invention.

Referring now to FIG. 1, there is shown a urinary collection system generally designated 10 having a receptacle 12, a first container 14, a second container 15, and clamping apparatus 16. The receptacle 12 has front and back walls 18 and 20 of suitable flexible plastic material joined at their periphery to define a collection chamber 22 between the front and back walls 18 and 20. The receptacle 12 may have a vent 24 communicating between the chamber 22 and the atmosphere with a bacteria filter to prevent passage of bacteria into the chamber 22. The receptacle 12 has a connector 26 in the form of a drip chamber attached to an upper portion of the front wall 18 and communicating with the chamber 22. The system 10 has an elongated drainage tube 28 having a downstream end 30 attached to the connector 26, such that the drainage tube 28 communicates with the collection chamber 22 through the connector 26. The receptacle 12 also has a tubular section 32 of flexible elastic material having an inner end 34 attached to a lower portion of the front wall 18, such that the tubular section 32 communicates with the collection chamber 22.

In use, a distal end of a catheter (not shown) is inserted through the urethra of patient until the distal end of the catheter is located in the patient's bladder, with a proximal end of the catheter located outside the patient's body. An upstream end of the drainage tube 28 is connected to the proximal end of the catheter. Urine drains through a drainage eye in the distal end of the catheter, through the catheter and drainage tube 28 into the collection chamber 22 for retention therein. It has been found that bacteria has a tendency to grow in the environment of the collected urine in the collection chamber 22, and may pass by retrograde movement through the drainage tube 28 and catheter into the patient's bladder with possible harmful results to the patient. The present invention is directed to a device to minimize the possibility of bacteria growth in the collection chamber 22.

The second container 15 has a front wall 36 and a back wall 38 of flexible plastic material joined at their periphery to define a holding chamber 40. As shown, the second container 15 is located above the receptacle 12.

The first container 14 has a front wall 42 and a back wall 44 of flexible plastic material joined at their periphery to define a supply chamber 46 to retain a supply of a liquid bactericide, such as chlorhexidine gluconate. As shown, the first container 14 is located above the second container 15. The system 10 may have a cord 48 to support the first container 14 from a suitable object, such as a bed rail.

Figure 2:
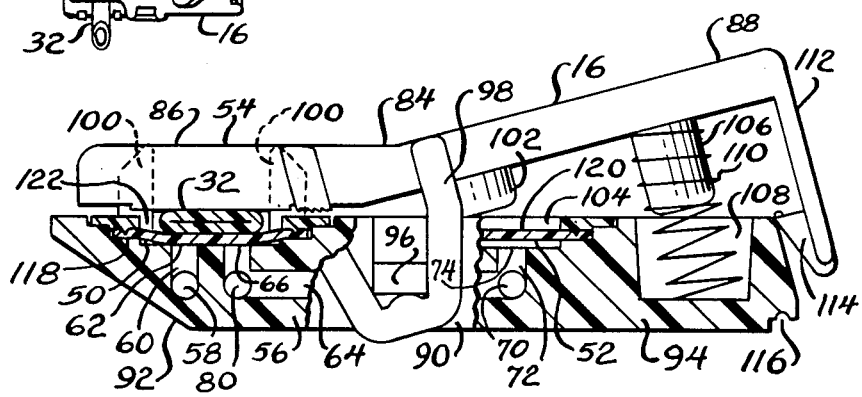
FIG. 2 is a fragmentary sectional view of clamping apparatus in the collection system, with the clamping apparatus being in a position closing a tubular section of a receptacle in the system.
Figure 3:
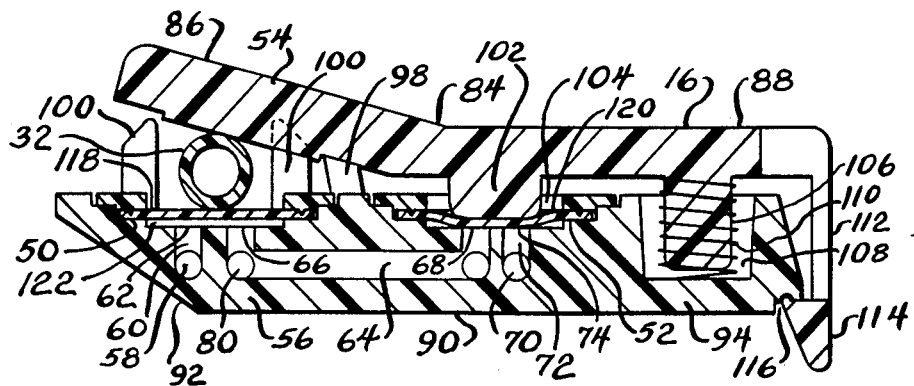
FIG. 3 is a sectional view of the clamping apparatus in another position with the tubular section open.

With reference to FIGS. 2 and 3, the clamping apparatus 16 has a first valve member 50 and a second valve member 52. The clamping apparatus 16 has a first clamp member 54 and a second clamp member 56, with the first and second valve members 50 and 52 being located in the second clamp member 56. The second clamp member 56 has an opening 58 which communicates through a passageway 60 with a port 62 of the first valve member 50. The second clamp member 56 has a passageway 64 which communicates between a port 66 of the first valve member 50 and a port 68 of the second valve member 52. Also, the second clamp member 56 has an opening 70 which communicates through a passageway 72 with a port 74 of the second valve member 52. With reference to FIGS. 1–3, the system 10 has a first conduit 76 which communicates between a lower portion of the supply chamber 46 and the opening 58 associated with the first valve nember 50. The system 10 has a second conduit 78 communicating between the holding chamber 40 and an opening 80 which communicates with the passageway 64. The system 10 also has a third conduit 82 which communicates between a lower portion of the collection chamber 22 and the opening 70 associated with the second valve member 52.

With reference to FIGS. 2 and 3, the first clamp member 54 has a central portion 84, a first end portion 86 extending from the central portion 84, and a second opposed end portion 88 extending from the central portion 84. The second clamp member 56 has a central portion 90, a first end portion 92 extending from the central portion 90, and an opposed second end portion 94 extending from the central portion 90. The second clamp member 56 has a pair of opposed side bosses 96 on the central portion 90. The first clamp member 54 has a pair of opposed side U-shaped portions 98 extending from the central portion 84. As shown, the bosses 96 are received in the U-shaped portions 98, such that the first clamp member 54 is pivotally mounted on the second clamp member 56. The clamping apparatus 16 is movable between a first position, as shown in FIG. 3, with the second end portions 88 and 94 being closely spaced and with the first end portions 86 and 92 being widely spaced, and a second position, as shown in FIG. 2, with the first end portions 86 and 92 being closely spaced and with the second end portions 88 and 94 being widely spaced.

The tubular section 32 is received between the first end portions 86 and 92 of the clamp members. The second clamp member 56 has a spaced pair of pins 100 on opposed sides of the tubular section 32 for a purpose which will be described below. The first clamp member 54 has a boss 102 adjacent the central portion 84 which is receivable in a cavity 104 of the second clamp member 56. The first clamp member 54 has a boss 106 on the second end portion 88 which is receivable in a cavity 108 in the second end portion 94 of the second clamp member 56. As shown, a helical spring 110 is trapped between the boss 106 and the cavity 108, such that the spring 110 is connected between the first and second clamp members 54 and 56, and such that the spring 110 biases the clamping apparatus 16 from the first position, as shown in FIG. 3, to the second position, as shown in FIG. 2. The first clamp member 54 has a flange 112 at the outer end of the second end portion 88, and a head 114 at the outer end of the flange 112, with the head 114 being receivable in a groove 116 at the outer end of the second end portion 94, such that the first and second clamp members 54 and 56 may be latched at the first position by placement of the head 114 in the groove 116. The head 114 may be removed from the groove 116 to permit movement of the clamp members 54 and 56 to the second position, as shown in FIG. 2.

The first valve member 50 comprises a sheet 118 of flexible elastic material received in a cavity 122 and extending across the ports 62 and 66 in the first end portion 92 of the second clamp member 56. With reference to FIG. 3, in the first position of the clamping apparatus 16, the first end portions 86 and 92 are widely spaced to permit opening of the tubular section 32 and movement of the sheet 118 from the ports 62 and 66 in order to establish communication between the ports 62 and 66. Thus, in this configuration of the clamping apparatus 16, the urine is drained through the open tubular section 32, and the bactericide passes from the supply chamber 46 through the first conduit 76, through the opening 58 and port 62, and beneath the sheet 118 through the port 66 to the passageway 64, after which it passes from the opening 80 through the second conduit 78 to the holding chamber 40. In this configuration, the pins 100 retain the tubular section 32 in place. In the second position of the clamping apparatus 16, with reference to FIG. 2, the first end portions 86 and 92 engage against the tubular section 32 in order to close the tubular section 32 and prevent passage of urine through the tubular section 32. Also, in this configuration, the tubular section 32 engages against the sheet 118, and moves the sheet 118 against the ports 62 and 66 in order to close the ports 62 and 66 and prevent passage of liquid through the first valve member 50. Thus, in this configuration, the first valve member 50 prevents passage of the bactericide from the holding chamber 40 to the supply chamber 46.

The second valve member 52 comprises a sheet 120 of flexible elastic material received in the cavity 104 and extending across the ports 68 and 74. With reference to FIG. 3, in the first position of the clamping apparatus 16, the boss 102 engages against the sheet 120 in order to close the ports 68 and 74 and prevent communication between the ports 68 and 74, thus closing the second valve member 52. Accordingly, in this configuration of the clamping apparatus 16, the second valve member 52 prevents passage of liquid between the holding chamber 40 and the collection chamber 22. With reference to FIG. 2, in the second position of the clamping apparatus 16, the boss 102 is spaced from the sheet 120, and the sheet 120 flexes away from the ports 68 and 74 to establish communication between the ports 68 and 74 and open the second valve member 52. In this configuration, the bactericide is permitted to pass from the holding chamber 40 through the second conduit 78, through the opening 80 and passageway 64, through the port 68 and beneath the sheet 120, through the port 74, and through the opening 70 and third conduit 82 into the collection chamber 22.

In use, the patient is catheterized, the clamping apparatus 16 is moved to the second position as shown in FIG. 2, and urine is permitted to collect over a period of time in the collection chamber 22 since the tubular section 32 is closed in this position of the clamping apparatus 16. When it is desired to empty the contents of the collection chamber 22, the second end portions 88 and 94 of the first and second clamp members 54 and 56 are moved toward each other, as shown in FIG. 3, and the head 114 is placed in the groove 116 in order to lock the first and second clamp members 54 and 56 in the first position. In this configuration, the tubular section 32 is opened to permit drainage of urine through the tubular section 32. Also, at this time, the first valve member 50 is opened to permit passage of a quantity of the bactericide from the supply chamber 46 to the holding chamber 40, while the second valve member 52 is closed to prevent passage of the contents of the collection chamber 22 into the holding chamber 40. When drainage of the collection chamber 22 has been completed, the head 114 is removed from the groove 116, and the second end portions 88 and 94 of the first and second clamp members 54 and 56 are released, such that the spring 110 moves the clamping apparatus 16 to the second position, as shown in FIG. 2. Again, in this configuration, the clamping apparatus 16 closes the tubular section 32. Also, at this time, the first valve member 50 is closed to prevent passage of the bactericide from the holding chamber 40 into the supply chamber 46, and the second valve member 52 is opened to permit passage of the bactericide from the holding chamber 40 into the collection chamber 22. Thus, in accordance with the present invention, a quantity of the bactericide is automatically introduced from the first container 14 into the receptacle 12 responsive to emptying of the collection chamber 22, and the bactericide introduced into the collection chamber 22 at the start of each collection period minimizes the possibility of bacteria growth in the collection chamber 22.

The foregoing detailed description is given for clearness of understanding only, and no unnecessary limitations should be understood therefrom, as modifications will be obvious to those skilled in the art.

I claim:

1. A collection system for body fluids, comprising:
   a receptacle having a collection chamber for retaining the body fluids and a discharge line;
   a first container having a supply chamber and a discharge line;
   a bactericide in the supply chamber;
   a second container having a supply and discharge line and a holding chamber, said holding chamber being located above a lower portion of the collection chamber, and said supply chamber being located above a lower portion of the holding chamber; and
   a two position clamp having first and second valve means each movable to a closed position, said first valve shutting off the discharge line from the collection chamber and the discharge line from said first container, said second valve shutting off supply from the second container to the collection chamber and means for opening said first valve means while closing said second valve means and for closing said first valve means while opening said second valve means 2. The system of claim 1 wherein the first valve means prevents the passage of bactericide from the holding chamber into the supply chamber.

3. The system of claim 1 wherein the second valve means prevents the passage of the contents of the collection chamber into the holding chamber.

4. The system of claim 1 wherein the second container is located above the receptacle, and the first container is located above the second container.

5. The system of claim 1 including a first line communicating between the supply chamber and the first valve means, a second line communicating between the holding chamber and intermediate the first and second valve means, and a third line communicating between the collection chamber and the second valve means.

6. The system of claim 1 including means for biasing the first valve means closed.

7. The system of claim 1 including means for latching the first valve means open.

8. A collection system for body fluids, comprising:
   a receptacle having a collection chamber for retaining the body fluids, and a drainage tubular section of flexible material communicating with the collection chamber;
   a first container having a supply chamber;
   a bactericide in the supply chamber;
   a second container having a holding chamber, said holding chamber being located above a lower portion of the collection chamber, and said supply chamber being located above a lower portion of the holding chamber;
   clamping apparatus comprising first and second clamp members, including means for pivoting central portions of the first and second clamp members, with first and second end portions of the first and second clamp members extending from said central portions, said tubular section being received between the first end portions of the first and second clamp members, said clamping apparatus being movable between a first position with the first end portions being substantially spaced such that said tubular section is substantially open and said second end portions being closely spaced, and a second position with said first end portions being closely spaced and engaging against said tubular section to close the tubular section and with said second end portions being substantially spaced;
   first valve means opening to permit passage of the bactericide from the supply chamber to the holding chamber responsive to movement of the clamping apparatus to said first position, and closing responsive to movement of the clamping apparatus to said second position; and second valve means opening to permit passage of the bactericide from the holding chamber into the collection chamber responsive to movement of the clamping apparatus to said second position, and closing responsive to movement of the clamping apparatus to said first position.

9. The system of claim 8 including means for biasing the clamping apparatus from said first position to said second position.

10. The system of claim 9 wherein the biasing means comprises a spring extending between the second end portions of the first and second clamp members.

11. The system of claim 9 including means for latching the first and second clamp members at said first position.

* * * * *